United States Patent [19]
Schreier et al.

[11] Patent Number: 5,973,135
[45] Date of Patent: *Oct. 26, 1999

[54] DNA COMPRISING PLUM POX VIRUS AND TOMATO SPOTTED WILT VIRUS CDNAS FOR DISEASE RESISTANCE

[75] Inventors: Peter Helmut Schreier, Köln; Klaus Stenzel, Düsseldorf; Günter Adam, Braunschweig; Edgar Maiss, Braunschweig, all of Germany

[73] Assignee: Bayer Aktiengesellschaft, Leverkusen, Germany

[*] Notice: This patent is subject to a terminal disclaimer.

[21] Appl. No.: 08/711,728

[22] Filed: Sep. 3, 1996

Related U.S. Application Data

[62] Division of application No. 08/247,809, May 23, 1994, Pat. No. 5,569,823.

[30] Foreign Application Priority Data

May 28, 1993 [DE] Germany ............................ 43 17 845

[51] Int. Cl.⁶ .................. A01H 1/00; C07H 21/04; C07K 14/005; C12N 5/14
[52] U.S. Cl. .................. 536/23.72; 536/23.1; 435/69.1; 435/172.3; 435/240.4; 435/320.1; 435/6; 800/279; 800/280
[58] Field of Search ................ 435/6, 69.1, 172.3, 435/240.4, 320.1; 536/23.1, 23.72; 800/279, 280

[56] References Cited

PUBLICATIONS

E. Maiss, et al., "The complete nucleotide sequence of plum pox virus RNA", J. Gen. Virol., Bd. 70, 1989, pp. 513–524.
E. Maiss, et al., "Cloning and sequencing of the S RNA from a Bulgarian isolate of tomato spotted wilt virus", J. Gen. Virol., Bd. 72, 1991, pp. 461–464.
M. Ravelonandro, et al., "Variable resistance to plum pox virus and potato virus Y infection in transgenic Nicotiana plants expressing plum pox virus coat protein", Plant Sci., Bd. 91, 1993, pp. 157–169.
P. de Haan, et al., "Characterization of RNA–mediated resistance to tomato spotted wilt virus in transgenic tobacco plants", Bio/Technology, Bd. 10, 1993, pp. 1133–1137.
M. Prins et al., *MPMI*, 8: 85–91 (1995).
Gielen et al., (1991) Bio/Technology 9: 1363–1367.
de Haan et al., (1989) J.Gen.Virol. 70: 3469–3473.
de Haan et al, (1992) Bio/Technology 10: 1133–1137.
Maiss et al., (1989) J.Gen.Virol. 70: 513–524.
Maiss et al., (1991) J.Gen.Virol. 72: 461–464.
Wilson (1993, Apr.) Proc.Natl.Acad.Sci USA 90: 3134–3141.
Nejidat et al., (1990) Physiologia Plantarium 80: 661–668.

*Primary Examiner*—Jeffrey Stucker
*Assistant Examiner*—Phuong T Bui
*Attorney, Agent, or Firm*—Sprung Kramer Schaefer & Briscoe

[57] ABSTRACT

The present invention relates to novel, recombinant deoxyribonucleic acids (DNA), to vectors and host organisms which contain them, and to transgenic plants which contain the recombinant DNA and possess an elevated resistance toward pernicious organisms and plant diseases, where the recombinant deoxyribonucleic acids (DNA) are characterized in that they consist of a combination of the following components, or components possessing a DNA which in each case has the same effect, or contain these constituents:

(a) a double-stranded cDNA fragment which is derived from the RNA of the plum pox virus (PPV) ("fragment A"), and (b) a double-stranded cDNA fragment which is derived from the S RNA of the tomato spotted wilt virus (TSWV) ("fragment B"), it being possible for these combinations also to possess, in addition to further DNA fragments which may optionally be present, a promoter which is active in plant cells.

**24

DNA COMPRISING PLUM POX VIRUS AND TOMATO SPOTTED WILT VIRUS CDNAS FOR DISEASE RESISTANCE

This application is a divisional, of application Ser. No. 08/247,809, filed May 23, 1994, now U.S. Pat. No. 5,569,823.

The present invention relates to novel, recombinant deoxyribonucleic acids (DNA), to vectors and host organisms which contain them, and to transgenic plants which contain the recombinant DNA and exhibit increased resistance toward pernicious organisms and plant diseases.

For a number of viruses, it has already been shown that when either structural or non-structural genes are isolated from these viruses and induced, in a suitable manner, to express in transgenic plants, they give rise, in the plants, to increased resistance toward infection by the homologous virus or to attenuation and/or slowing down of symptom manifestation. This was demonstrated for the first time using the example of the coat protein of tobacco mosaic virus (TMV) (EP-A2-0 223 452; Beachy et al., 1985; and Powell Abel et al., 1986). TMV belongs to the Tobamovirus genus and has a comparatively simple architecture and, for its genetic information, possesses, like many other plant viruses, a single-stranded RNA molecule having plus-strand information (single-stranded positive-sense RUA genome). The genetic information is packaged in a coat which consists of many identical subunits. Later on, it was possible to show that a comparable strategy also succeeded in the case of the tomato spotted wilt virus (TSWV), which is a virus which is essentially different and belongs to the Tospovirus genus of the Bunyaviridae family (EP-A1-0 426 195; Gielen et al., 1991; De Haan et al., 1992). The genus Tospovirus is classified as having a morphologically spherical particle of about 100 nm in diameter and a three-partite, single-stranded RNA genome, which, as a nucleoprotein complex (nucleocapsid), is surrounded by a lipid coat. This lipid coat is charged with glycoproteins.

The three-partite genome possesses ambisense or minus-strand information (single-stranded RNA molecules of negative or ambisense polarity, De Haan et al., 1990). In this case, resistance in transgenic plants is based on transferring the N structural gene of a tospovirus, the tomato spotted wilt virus (=TSWV) into a plant, where it is expressed. The N gene product is a component of the abovementioned nucleoprotein complex.

Whereas it was possible to demonstrate pronounced cross resistance toward closely related tobamoviruses in the case of the TMV coat protein (e.g. Tuner et al., 1987), such cross resistance is not so far known in the case of TSWV and expression of the N gene (De Haan et al., 1992; MacKenzie and Ellis, 1992; Sheng-zi et al., 1992).

Novel recombinant deoxyribonucleic acids (DNA) have been found, which are characterized in that they consist of, or contain, a combination of the following components or components possessing a DNA which is in each case of equal effect:

(a) a double-stranded cDNA fragment which is derived from the RNA of the plum pox virus (PPV) ("fragment A"), and (b) a double-stranded cDNA fragment which is derived from the S RNA of tomato spotted wilt virus (TSWV) ("fragment B"), it being possible for this combination to also possess, in addition to further DNA fragments which may optionally be present, a promoter which is active in plant cells.

It has furthermore been found that transgenic plants which have the novel recombinant DNA integrated in their genome (and express this DNA) exhibit increased resistance toward pernicious organisms and plant diseases.

The transgenic plants also, and in particular, demonstrate increased resistance not only toward the homologous TSW virus isolate, from which fragment B was derived, but also toward other tospovirus species. This is surprising, since the recombinant deoxyribonucleic acids which are known from the state of the art and which were derived from naturally occurring viral genes do not have any such broad effect in the corresponding transgenic plants (De Haan et al., 1992; MacKenzie and Ellis, 1992). In addition to this, it is particularly surprising that increased resistance can be observed toward viruses which do not belong to the Tospovirus genus.

In the recombinant DNA according to the invention, fragment B is situated after (i.e. in the 3' direction) fragment A, with the two fragments being connected to each other either directly or by an additional DNA fragment ("fragment C"). A promoter which is active in plants is placed upstream of fragment A when the DNA according to the invention represents a complete transcription unit. In this case, fragment B is also followed by a 3' untranslated DNA which is connected to fragment B either directly or via an additional DNA fragment ("fragment D"). The 3' untranslated DNA contains a transcription termination sequence (TTS) and a polyadenylation site.

The term "transcription termination sequence" denotes that this is a sequence which defines the end of the RNA synthesis, by a particular polymerase from a particular DNA sequence serving as the template. In the case of the "chimeric genes" which are employed in transgenic plants, the TTS of the nopaline synthase gene (Zambryski et al., 1983), the octopine synthase gene (Herrera-Estrella et al., 1983) or the 35S transcript of CaMV (cauliflower mosaic virus) (Pietrzak et al., 1986) may, for example, be used.

In addition, the term "polyadenylation site" or "polyadenylation signal" preferably denotes a sequence consisting of six nucleotides (e.g. AAUAAA) which effects exact processing of the primary transcript and post-transcriptional synthesis of a "poly-A sequence" on the 3' end of the primary transcript.

From this, it follows, consequently, that a complete transcription unit has the following DNA arrangement:

(5') Promoter - fragment A - optionally: fragment C - fragment B - optionally: fragment D - 3' untranslated DNA (3')

The DNA arranged in this way is a part of the present invention. The following arrangements of recombinant DNA are likewise a constituent part of the present invention:

(5') Fragment A - optionally: fragment C - fragment B - optionally: fragment D - 3' untranslated DNA (3'), and Fragment A - optionally. fragment C - fragment B -optionally: fragment D (3'), and (5') Promoter - fragment A - optionally: fragment C - fragment B (3')

Fragment A is a double-stranded cDNA which is derived from the RNA of a plum pox virus (PPV), the term "derived" denoting that the cDNA is a DNA which is present in a form complementary to the virus RNA.

A DNA as reproduced in SEQ ID No:7 is preferably used as fragment A.

Fragment B is a double-stranded cDNA which is derived from S RNA, preferably from the N structural gene of tomato spotted wilt virus (TSWV), preferably the L3 isolate, the term "derived" denoting that the cDNA is a DNA which is present in a form complementary to virus RNA. A DNA as reproduced in SEQ ID No:11 is preferably used as fragment B.

Fragments A and B can be connected to each other either directly or, preferably, by a double-stranded DNA fragment C. A synthetic DNA fragment can be used as fragment C, which DNA fragment is selected such that it does not contain a stop codon in any particular reading frame, and connects fragments A and B such that they form an uninterrupted open reading frame which begins in fragment A and ends at the end of fragment B and in this way encodes a polypeptide.

Fragment C can preferably contain up to 134 nucleotides. Particularly preferably, fragment C contains 2 to 68 nucleotides. The synthetic DNA whose sequence is reproduced in SEQ ID No:9 is very particularly preferred as fragment C. This fragment connects the open reading frame beginning in fragment A with that of fragment B in a particularly advantageous manner.

All those promoters which are active in plants are suitable for use as promoters which can be located upstream of fragment A. Among these, those may be selected for special mention which are controlled by polymerase II, as may those which are under the control of polymerase III. Promoters which originate from phytopathogenic viruses are also selected for special mention. Among these, the 35S promoter of cauliflower mosaic virus (CaMV) is particularly preferred. Its sequence is reproduced in SEQ ID No:3. It is preferably, connected directly to fragment A.

All appropriate regions which bring about polyadenylation and transcription termination in plants can be employed as 3' untranslated DNA which contains a polyadenylation site and a TTS signal and follows fragment B, with fragment D optionally being interpolated. 3' Untranslated DNA sequences from phytopathogenic viruses are preferably selected. The 3' untranslated CaMV 35S DNA, whose sequence is depicted in SEQ ID No:4, is particularly preferably used.

The above described fragments can in each case be replaced in the recombinant DNA according to the invention by corresponding fragments containing DNA having the same effect. In the DNA having the same effect, 1 or more bases, or 1 or more codons, can be missing or be replaced by other bases or codons, it being possible, however, to alter the fragments only to the extent that their effect is essentially preserved, i.e. that the combinations of fragments according to the invention lead in plants to elevated resistance toward pernicious organisms and plant diseases. Any DNA can be considered as DNA having the same effect which can be hybridized under stringent conditions with a single-strand DNA according to SEQ ID No:1–13 and which, in combination with the remaining fragments, brings about the desired increase in resistance in plants. DNA having the same effect is preferably a DNA from which the same polypeptides, or polypeptides "having the same effect" can be "derived", as from the DNA sequences according to SEQ ID: 1, 5, 7, 9 and 11 (cf. the protein sequences according to SEQ ID: 2, 6, 8, 10 and 12, as well). In this instance, derived denotes that a DNA can be transcribed into RNA, which can be translated into protein. Polypeptides having the same effect means that they are polypeptides whose total primary sequence has the same effect, it being possible, however, to exchange individual amino acids without changing the secondary, tertiary or quaternary structure in such a way that the desired increase in resistance is lost. DNA according to SEQ ID No:7 and 11 can also be employed as a probe in order to isolate appropriate additional fragments from plum pox viruses or tospo-viruses that can be used in accordance with the invention. Using these probes, the fragments can also be detected, in a customary manner, in vectors or in the plant genome. In accordance with the invention, that recombinant DNA is preferred which contains at least one of the fragments A or B having the sequence according to SEQ ID No:7 or 11, or a corresponding DNA having the same effect.

In accordance with the invention, that recombinant DNA is particularly preferred which contains both fragment A and fragment B having the sequences according to SEQ ID No:7 and 11, or a corresponding DNA having the same effect.

In accordance with the invention, that recombinant DNA is very particularly preferred which has the sequence according to SEQ ID No:1, including the corresponding DNA having the same effect. That recombinant DNA which has the sequence according to SEQ ID No:5, or a corresponding DNA having the same effect, is very particularly preferred as a complete transcription unit.

The DNA fragments which are useable in accordance with the invention, as well as the DNA according to the invention, can be obtained by the customary methods with the aid of the information in SEQ ID No:1–13. In addition to this, cDNA fragments of the plum pox virus (PPV) genome which are usable in accordance with the invention, as well as cDNA fragments of the S RNA genome of the TSW virus, can be obtained from the Deutsche Sammlung von Mikroorganismen und Zellkulturen (German Collection of Microorganisms and Cell Cultures) (DSM) under the numbers PL-1080 (pPPV-NAT 5'-4) and PL-1081 (pTSW L3-308). Different cDNA's of the "Strassburg isolate" and of the CM1841 isolate (ATCC No. 45031) of CaMV can likewise be obtained from the DSM under the numbers PL-1029 and PL-1033 (cf. DSM order list, plant virus group, Messeweg 11/12, W-3300 Braunschweig, Federal Republic of Germany).

The plasmids PL-1080 and PL-1081 have been deposited in *Escherichia coli* at the German Collection of Microorganisms (DSM), Mascheroder Weg 1b, D-3300 Braunschweig, Federal Republic of Germany, in conformity with the regulations of the Budapest Treaty on the international recognition of the deposition of microorganisms for the purposes of patent processes:

| DSM reference designation | Entry Number | Date of deposition |
|---|---|---|
| BY-1080 (contains PL-1080) | DSM 8276 | 07.05.1993 |
| BY-1081 (contains PL-1081) | DSM 8277 | 07.05.1993 |

The recombinant DNA according to the invention does not occur in nature. It can be obtained by the person skilled in the art with the aid of the customary methods of molecular biology (Sambrook et al., 1989) using the information contained in the preceding description, in particular using SEQ ID No:1 to 13.

The present invention also relates to novel vectors, in particular plasmids or phages, which contain the recombinant DNA according to the invention, e.g. (as described below) the plasmids pSLTSWVL3 and pXLTSWVL3. The present invention also relates to novel host organisms, in particular microorganisms, which contain the recombinant DNA according to the invention, preferably integrated into the plasmid. The *Escherichia coli* and *Agrobacterium tumefaciens* strains which are customarily used are particularly suitable for use as microorganisms. The *Agrobacterium tumefaciens* strain XLTSWVL3, which is described in more detail below and which contains the plasmid pXLTSWVL3, may be mentioned by way of example.

The vectors and microorganism strains can be obtained by the person skilled in the art with the aid of the customary methods of molecular biology and using the information contained in the preceding description, particularly using Seq ID No: 1 to 13.

The recombinant DNA according to the invention can be inserted into the genome of plants, as a result of which these transgenic plants are rendered more highly resistant toward pernicious organisms and plant diseases.

The elevated resistance of the transformed plants is of importance for agriculture and forestry, for the cultivation of ornamental plants and medicinal plants, and for plant breeding. It is also advantageous in the cultivation of plant cells, e.g. for isolating pharmaceutically utilizable substances, to have plant cells available which exhibit elevated resistance against infection by microbial pests, in particular fungi and viruses.

Consequently, the present invention also relates to a process for preparing transgenic plant cells (including protoplasts) and plants (including plant parts and seeds) having increased resistance to pernicious organisms and plant diseases, which process is characterized in that (a) the DNA according to the invention is introduced once or more than once into the genome of plant cells (including protoplasts) and, where appropriate, (b) whole, transformed plants are regenerated from the transformed plant cells (including protoplasts) and, where appropriate, multiplied, and, where appropriate, (c) the desired plant parts (including seeds) are isolated from the transgenic plants of the parental generation which result in this way, or from further generations obtained therefrom, and, (d) where appropriate, the genome of the transgenic plants is, in order to produce further plants, combined with the genome of other plants, and the descendants multiplied.

The process steps (a), (b) and (c) can be carried out in a customary manner in accordance with the known processes and methods.

Transgenic plant cells (including protoplasts) and plants (including plant parts and seeds) which contain one or more copies of the DNA according to the invention, as well as such transformed plant cells and plants which can be obtained by the above processes, are likewise included in the present invention.

(a) The use of the recombinant DNA according to the invention for increasing the resistance of plants toward pernicious organisms and plant diseases, (b) the use of the recombinant DNA according to the invention for producing plant cells, plants, plant parts and plant multiplication material having an elevated resistance toward pernicious organisms and plant diseases, and (c) the use of the transgenic plants according to the invention (including plant parts and plant seeds) for producing multiplication material and for producing novel plants and their multiplication material are also parts of the present invention.

Plants (including plant cells, plant parts and multiplication material) are also part of the present invention which contain the protein according to SEQ ID No: 2 or 6, respectively, or, where appropriate, contain a protein according to SEQ ID No: 2 or 6, respectively, which is truncated at the aminoterminus.

A number of different methods are available for inserting the recombinant DNA according to the invention into the genetic material of plants or plant cells. The transfer of DNA can be effected in accordance with the customary and well-known methods, the person skilled in the art being able to ascertain without difficulty the appropriate method in each case. The DNA according to the invention, which is to be used for transforming plants, must contain an appropriate promoter which is active in plants and a 3' untranslated region. The recombinant DNA according to SEQ ID No:5 is particularly suitable.

The Ti plasmid of *Agrobacterium tumefaciens* is available as a particularly favorable vector of wide applicability for transferring foreign DNA into the genomes of dicotyledonous and monocotyledonous plants. The DNA according to the invention is, together with regulatory DNA sequences, inserted into the T DNA of appropriate Ti plasmids (e.g. Zambryski et al., 1983) and transferred by infection of the plant, infection of plant parts or plant tissues, such as, for example, leaf disks, stalks, hypocotyls, cotyledons or meristems, or tissue derived therefrom, such as, for example, secondary embryos and calluses, or by coculturing protoplasts with *Agrobacterium tumefaciens*.

An alternative is to incubate the DNA in plant protoplasts (e.g. Hain et al., 1985; Krens et al., 1982; Paszkowski et al., 1984) in the presence of polycations or calcium salts and polyethylene glycol.

Uptake of the DNA can also be additionally encouraged by using an electrical field (electroporation) (e.g. Fromm et al., 1986).

The DNA can also be introduced in a known manner by way of plant pollen, with the pollen being "bombarded" with physically accelerated particles which harbor the DNA (cf. EP-A 0 270 356).

The plants are regenerated in a known manner using appropriate nutrient media (e.g. Nagy and Maliga 1976).

In a preferred embodiment of the process according to the invention (according to the method from EP-A 116 718), the recombinant DNA according to the invention is cloned, in isolated form, into a suitable intermediate *E.coli* vector, e.g. pGV700 or pGV710 (cf. EP-A 116 718), or preferably derivatives thereof which additionally contain a reporter gene such as nptII (Herrera-Estrella et al. 1983) or hpt (Van den Elzen et al. 1986), for example.

The plasmid constructed in this way is transferred by customary methods (e.g. Van Haute et al. 1983) into *Agrobacterium tumefaciens* which contains, for example, pGV 3850 or derivatives thereof (Zambryski et al. 1983). As an alternative, the DNA according to the invention can be cloned in a binary vector, e.g. pCV001 or pCV002 (e.g. Koncz and Schell 1986), and then transferred, as described above, into a suitable Agrobacterium strain (Koncz and Schell 1986). The resulting Agrobacterium strain, which contains the recombinant DNA in a form which is transferrable to plants, is subsequently used for the plant transformation.

In a further preferred embodiment, the recombinant DNA is transferred into plant protoplasts, where appropriate together with another plasmid which contains a reporter gene for plant cells, e.g. for kanamycin resistance (e.g. Herrera-Estrella et al. 1983) or a hygromycin resistance (van den Elzen, 1986), preferably pLGV neo 2103 (Hain et al., 1985), pMON 129 (Fraley R. T. et al., Proc. National Acad. Sci. USA 80, 4803 (1983)), pAK 1003, pAK 2004 (Velten J. et al., EMBO Journ. Vol. 3, 2723 (1984)) or pGSST neo 3 (pGSST3) (EP-A-189 707), by direct gene transfer in a customary manner (e.g. Hain et al 1985). In this context, the plasmid(s) can be present in circular form, although linear form is preferred. When a plasmid containing a reporter gene is used, kanamycin-resistant protoplasts are then examined for expression of the recombinant DNA. In the alternative case (without reporter gene) the resulting calluses are tested for expression of the recombinant DNA (screening using customary methods).

Transgenic plants or plant cells are produced in accordance with known methods, e.g. by transformation of leaf disks (e.g. Rorsch et al. 1985), by coculture of regenerating plant protoplasts or cell cultures with *Agrobacterium tumefaciens* (e.g. Marton et al. 1979, Hain et al. 1985) or by direct DNA transfection. Transformed plants which result are detected either by selecting for expression of the reporter gene, e.g. by phosphorylating kanamycin sulfate in vitro (Reiss et al. 1984; Schreier et al. 1985) or by the expression of nopaline synthase (in accordance with Aerts et al. 1983) or of the recombinant DNA according to the invention by Northern blot analysis and Western blot analysis. The gene products of the recombinant DNA can also be detected in transformed plants in a known manner using specific antibodies (Adam et al. 1987, 1991).

The transformed plant cells are cultivated and regenerated to form whole plants in accordance with the usual methods using the nutrient media which are appropriate in each case.

Both the transformed plant cells and the transformed plants, which contain the DNA according to the invention and which are constituent parts of the present invention, exhibit a considerably higher degree of resistance to pernicious organisms and plant diseases, in particular to nematodes, phytopathogenic fungi and viruses.

In connection with the present invention, the expression "plants" denotes both whole plants and plant parts, such as leaves, seeds, tubers, cuttings, etc. "Plant cells" include protoplasts, cell lines, plant calluses, etc. "Multiplication material" denotes plants, plant parts, such as seeds, tubers and cuttings, as well as plant cells, which can be used for multiplying the transgenic plants and plant cells, and is consequently likewise a part of the present invention.

Practically all plants are included in those plants which can be imparted elevated resistance toward pests by the incorporation (transformation) of the recombinant DNA according to the invention. There is, naturally, a particular requirement for producing resistance in the case of the cultivated plants, such as forestry plants, e.g. spruces, fir trees, Douglas firs, pines, larches, beech trees and oak trees, as well as plants which provide nutrients and raw materials, e.g. cereals (in particular wheat, rye, barley, oats, millet, rice and maize), potatoes, leguminous plants (such as pulses and, in particular, alfalfa and soya beans), vegetables (in particular cabbage species and tomatoes), fruit (in particular apples, pears, cherries, grapes, citrus fruits, pineapples and bananas), oil palms, tea, cacao and coffee bushes, tobacco, sisal and cotton, as well as in the case of medicinal plants, such as Rauwolfia and Digitalis. Potatoes, tomatoes, leguminous plants and Curcubitaceae may be particular preferably mentioned.

Animal pests, such as insects, mites and nematodes, as well as microbial pests, such as phytopathogenic fungi, bacteria and viruses, may be mentioned as pests (pernicious organisms and organisms which elicit plant diseases) against which elevated resistances may be achieved according to the invention. Those which are selected for special mention are plant-damaging nematodes and microbial pests, in particular phytopathogenic fungi and viruses.

The pernicious insects include, in particular insects of the orders:
Orthoptera, Dermaptera, Isoptera, Thysanoptera, Heteroptera, Homoptera, Lepidoptera, Coleoptera, Hymenoptera and Diptera.
The pernicious mites include, in particular:
Tarsonemus spp., Panonychus spp. and Tetranychus spp.

The plant-parasitizing nematodes include Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp., The microbial pests include, in particular, the phytopathogenic fungi:
Plasmodiophoromycetes, Oomycetes, Chytridiomycetes, Zygomycetes, Ascomycetes, Basidiomycetes, Deuteromycetes.

The phytopathogenic bacteria include, in particular the Pseudomonadaceae, Rhizobiaceae, Enterobacteriaceae, Corynebacteriaceae and Streptomycetaceae.

The virus diseases include, in particular, mosaic, dwarfing and yellowing viroses, and viroses which are elicited by tospoviruses.

Some causative agents of viral, fungal and bacterial diseases which come under the generic names listed above may be mentioned as examples, but not by way of limitation:
Barley yellow dwarf virus (BYDV), potato virus Y (PVY), cucumber mosaic virus (CMV), watermelon mosaic virus (WMV), tristeza virus, tobacco mosaic virus (TMV), tobacco necrosis virus (TNV), beet necrotic yellow vein virus (BNYVV) and, in particular, tomato spotted wilt virus (TSWV), all the tospoviruses, tobacco mosaic virus (TMV) and other tobamoviruses, and tobacco rattle virus and other tobraviruses.

Xanthomonas species, such as, for example, *Xanthomonas campestris* pv. *oryzae;*
Pseudomonas species, such as, for example, *Pseudomonas syringae* pv. *lachrymans;*
Erwinia species, such as, for example, *Erwinia amylovora;*
Pythium species, such as, for example, *Pythium ultimrum;*
Phytophthora species, such as, for example, *Phytophthora infestans;*
Pseudoperonospora species, such as, for example, *Pseudoperonospora humuli* or *Pseudoperonospora cubense;*
Plasmopara species, such as, for example, *Plasmopara viticola;*
Peronospora species, such as, for example, *Peronospora pisi* or *P. brassicae;*
Erysiphe species, such as, for example, *Erysiphe graminis;*
Sphaerotheca species, such as, for example, *Sphaerotheca fuliginea;*
Podosphaera species, such as, for example, *Podosphaera leucotricha;*
Venturia species, such as, for example, *Venturia inaequalis;*
Pyrenophora species, such as, for example, *Pyrenophora teres* or *P. graminea* (conidia form: Drechslera, syn: Helminthosporium);
Cochliobolus species, such as, for example, *Cochliobolus sativus* (conidia form: Drechslera, syn: Helminthosporium);
Uromyces species, such as, for example, *Uromyces appendiculatus;*
Puccinia species, such as, for example, *Puccinia recondita;*
Tilletia species, such as, for example, *Tilletia caries;*
Ustilago species, such as, for example, *Ustilago nuda* or *Ustilago avenae;*
Pellicularia species, such as, for example, *Pellicularia sasakii;*
Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

In addition, *Helminthosporium carbonum* may be listed.

Literature

Adam G., Chagas C. M., Lesemann D. E.; (1987) *J. of Phytopathology* 120, 31–43

Adam G., Lesemann D. E., Vetten H. J. (1991) *Ann. appl. Biol.* 118, 87–114

Aerts M. et al., Plant Sci. Lett. 17 (1993), 43–50

Beachey R. N., Chen Z-L., Horsch R. B., Rogers S. G., Hoffmann N. J. and Fraley R. T. (1985) *EMBO J*4, 3047–3050 de Avila A. C., de Haan P., Kormelink R., Resede RdeO., Goldbach R. W., and Peters D. (1993) *J. of Gen. Virol.* 74, 153–159

Chomezynski et al., Anal. Bioch. 162 (1987), 156–159 de Haan P., Wagemakers L., Peters D. and Goldbach R. (1990) *J. Gen. Virol.* 71, 1001–1007 de Haan P., Gielen J. J. L., Prins M., Wijkamp I. G., van Schepen A., Peters D., van Grinsven M. Q. J. M. and Goldbach R. (1992) *Bio/technologie* 10, 1133–1137

Fromm M. E. et al., Nature 319 (1986), 791–793

Gielen J. J. L., de Haan P., Kool A. J., Peters D., van Grinsven M. Q. J. M. and Goldbach R. (1991) *Bio/technologie* 9, 1363–1367

Goodall et al., Meth. in Enzym. 181 (1990), 148–161

Goodall and Filipowicz, Cell 58 (1989), 473–483

Herrea-Estrella L. et al., Nature 303 (1983), 209–213

Hain R. et al., Molec. Gen. Genet. (1985) 199, 161–168

Herrea-Estrella L. et al., EMBO J2 (1983), 987–995

Hoekema A., Hirsch P. R., Hooykaas P. J. J. and Schilperoort R. A. (1983) Nature 303, 179–180

Horsch R. B. et al., Science 277 (1985), 1229–1231

Krens F. H. et al., Nature 296 (81982), 72–74

Koncz C. and Schell J., Mol. Gen. Genet. 204 (1986), 338–396

Landsmann J., Llewwellyn D., Dennis E. S. and Peacock W. J. (1988) *Mol. Gen. Genet.* 214, 68–73

MacKenzie D. J. and Ellis P. J. (1992) *Molecular Plant-Microbe Interactions* 5, 34–40

Maiss E., Timpe U., Brisske A., Jelkmann W., Casper R., Himmler G., Mattanovich D. and Katinger H. W. D. (1989) *J. of Gen. Virol.* 70, 513–524

Maiss E., Ivanova L., Breyel E. and Adam G. (1991) *J. of Gen. Virol.* 72, 461–464

Maiss E., Timpe U., Brisske-Rode A., Lesemann D-E. and Casper R. (1992) *J. of Gen. Virol.* 73, 709–713

Marton L. et al., Nature (1979), 1229–1231

Mullis K. B. and Faloona F. A. (1987) *Methods Enzymol* 155, 335–350

Murashige T. and Skoog F., Physiol. Plant. 15 (1962), 47

Paszkowski J. et al., EMBO J3 (1984), 2717–2722

Pietrzak et al. (1986) *Nucleic Acid Res.* 14, 5857–5868

Powell Abel P. et al. (1986) *Science* 232, 738–743

Reiss B. et al., GENE 1081 (1984), 211–217

Sambrook J., Fritsch E. F. and Maniatis T. (1989) *Molecular Cloning a Laborarory manual,* 2nd Edition Schreier P. et al., EMBO J4 (1985), 25–32

Sheng-Zi et al. Phytopathology 82 (1992), 1223–1229

Steinecke et al., EMBO J11 (1992), 1525–1530

Töpfer R., Matzeit V., Gronenborn B., Schell J. and Steinbiss H. H. (1987) *Nucl. Acid Res.* 15, 5890

Tumer N. E., O'Connell K. M., Nelson R. S., Sanders P. R., Beachy R. N., Fraley R. T. and Shah D. M. (1987) *EMBO J*6, 1181–1188

Van den Elzen P. J. M. et al., Plant Mol. Biol. 5 (1985), 299–302

Van Haute E. et al., EMBO J2 (1983), 411–418

Velten J. et al., EMBO J12 (1984), 2723–2730

Zambryski et al., EMBO J. 2 (1983), 2143–2150.

The following examples are intended to clarify the present invention:

1. Construction of the recombinant DNA and transfer into agrobacteria:

As already explained, the present invention relates to a novel recombinant DNA, in particular a recombinant chimeric gene (SEQ ID No: 1), which is under the control of a promoter and contains a 3'-terminal sequence. The CaMV35S promoter (5' region) (SEQ ID No: 3) and the 3' untranslated region (SEQ ID No: 4) of the CaMV35S transcript are used here by way of example (Töpfer et al. 1987 and EP-A2-0 223 452). The entire example used here is shown in SEQ ID No: 5. The DNA (chimeric gene) (SEQ ID No: 1) according to the invention consists of several pieces which are joined in a particular sequence. It consists of a double-stranded cDNA fragment of 152 base pairs which was derived from the RNA of plum pox virus (PPV) (Maiss et al., 1989). This corresponds to the viral RNA sequence at positions 1–152 (SEQ ID No: 7) (Maiss et al., 1989). In this fragment, an open reading frame begins which is connected via a synthetic cDNA fragment (SEQ ID No: 9) to a cDNA fragment of the S RNA of the L3 isolate of the TSWV N gene (Maiss et al.; 1991) (SEQ ID No: 11). This connection is such that an open reading frame is generated which has an overall length of 956 bases without interruptions and which ends at position 992 of "SEQ ID No: 1". The subsequent cDNA sequence of the S RNA of the 3' non-translated region of TSWV (SEQ ID No: 11) is connected via a synthetic sequence (SEQ ID No: 13) to the 3' region of the 35S transcript of CaMV (SEQ ID No: 4) (Töpfer et al.; 1987).

The construction was effected using methods which are well-known and the details of which are described in (Sambrook, Fritsch and Maniatis, 1989).

The detailed procedure was as follows. A HindIII/-BamHI fragment of 454 base pairs in length from the commercially available plasmid pCaMVCN (Pharmacia) was cloned into the commercially available plasmid pT7T3 19U (Pharmacia) and termed pT7T3 35S. This novel plasmid was cut with SalI and the protruding ends filled in, and the DNA was then cut with EcoRI. A DraI/EcoRI fragment (572 base pairs in length), from the plasmid pPPV-NAT 5'4 (Maiss et al., 1989; Maiss et al. 1992), was then cloned into the plasmid thus prepared. This fragment contains a cDNA copy of the 5' end of PPV. The new plasmid was termed p35S 5'.16.

Using the synthetic oligonucleotide 5'-TGTGTTGAGTTTTATATTTCCTCTCCAAATG-AAA-3' (SEQ ID No: 14) which is complementary to the non-coding strand, the 3' end of the CaMV35S promoter sequence (5'- . . . AGAGG-3')(SEQ ID No: 15) was attached, with the aid of in-vitro mutagenesis, to the extreme 5' end (5'-AAAATAT . . . -3') (SEQ ID No: 16) of the cDNA of the PPV sequence. The new plasmid which resulted was termed p35S. A HincII fragment of 568 base pairs in length was isolated from this plasmid and cloned into the commercially available plasmid pT7T3 19U, which had been previously cut with SmaI and HincII. The designation of the resulting plasmid is pT7T3 19UPPVL. This plasmid was cut with EcoRV and SalI, and a fragment of 239 base pairs in length was isolated. This fragment was cloned into the EcoRV,XhoI cleavage sites of pRT101 (Töpfer et al. 1987). The resulting plasmid was termed pSL.

A BamHI/HindIII fragment was isolated from the plasmid pTSWV-L3/308 (Maiss et al.; 1991). The ends were filled in and inserted into the SmaI cleavage site of the vector pRT101 (Töpfer et al. 1987). The plasmid, which contains the inserted fragment in the correct orientation, was termed pSTSWVL3. An RsaI/-BamHI fragment of 868 base pairs in length was isolated from this plasmid, and cloned into the abovementioned vector pSL, which had been cut with SmaI and BamHI. The new plasmid which resulted was termed pSLTSWVL3. A fragment of 1716 base pairs in length, which contains the entire chimeric gene and the 5' and 3' untranslated regions of CaMV (35S), can be isolated from this latter plasmid using HindIII. This fragment was cloned into the plasmid pXL222 (Landsmann et al. 1988), which had been cut with HindIII. The resulting plasmid was termed pXLTSWVL3. This plasmid (pXLTSWVL3) was mobilized or transfected into the *A. tumefaciens* strain LBA 4404 (Hoekema et al. 1983). This new strain of Agrobacterium was termed XLTSWVL3.

2. Production of transgenic plants, and detection of the expression of the chimeric gene in these plants The Agrobacterium strain XLTSWVL3 was used for transforming plant cells or plant parts. The transgenic plants were selected on kanamycin-containing medium using a marker and selection gene, the gene for kanamycin resistance, which had been transferred at the same time. Twenty one individual candidates were chosen on the basis of their ability to express the chimeric gene. This involved firstly determining gene expression at the level of the mRNA. For this, the entire RNA isolated from transgenic plants was translated into cDNA using reverse transcriptase and the synthetic oligonucleotide 5'-GTC AGT GGC TCC AAT CCT GTC TGA AG-3' (SEQ ID No: 17), and the existence of mRNA of the chimeric gene was amplified with the aid of a second synthetic oligonucleotide 5'- TGT GGA GAA TTC GAG CTC GGT AC - 3' (SEQ ID No: 18) and the polymerase chain reaction (PCR; Mullis and Faloona, 1987), and identified as a fragment of 328 base pairs in length.

The twenty-one transgenic plants in which gene expression had been detected in the abovedescribed way and manner were next tested for production of the chimeric gene product using a specific antibody (ELISA) (Adam et al., 1987; 1991). The candidates XL4, XL8, XL11, XL14, XL15 and XL19 gave a clearly measurable signal and were selected for the initial, informatory phytopathological experiments.

In detail, the transformation of plants was carried out as follows.

2.1 Agrobacterium transformation

Leaf disks (Horsch et al., 1985) were used for transforming tobacco. For this purpose, leaves of about 2–3 cm in length from sterile shoot cultures were punched into disks of about 1 cm diameter and incubated together with a 24-hour cultivated Agrobacterium culture, after it had been taken up in 10 mM $MgSO_4$ and in 20 ml of MS medium (Murashige and Skoog, 1965), at 26° C. for about 60 hours. The leaf disks were subsequently washed 3× in MS medium containing 1000 μg/ml claforan, and then laid out on MS plates which contained 0.5 μg/ml NAA (naphthyl-acetic acid), 0.2 μg/ml BAP (benzylaminopurine) and 2% sucrose ("callus induction medium") and the appropriate selective agent (e.g. kanamycin sulfate), and incubated at 26° C. After 2 weeks on each occasion, the leaf disks were transferred to fresh callus induction medium. Once small calluses could be distinguished, they were transferred to shoot induction medium, which corresponds to the callus induction medium but contains 0.2 μg/ml NAA and 0.5 μg/ml BAP. Once the regenerated shoots had reached a length of 2–3 cm, they were transferred, for root induction, to MS medium which contained 1% sucrose but no hormones, and cultivated under sterile conditions at 24–26° C. (12 hrs. of light (1000–3000 lux), 12 hrs. in the dark). After. 4 to 6 weeks, the shoot cultures were transferred to fresh medium, grown into plants and subsequently cultivated under suitable conditions in a greenhouse.

For transforming potato plants, a further incubation of two days in the dark took place following incubation of the excised leaf disks in the Agrobacterium suspension. The leaf disks were then incubated for 8 days with 16-hour illumination on MS plates which contained 1.6% glucose, 5 mg/l NAA, 0.1 mg/l BAP, 500 mg/l claforan and the appropriate selective agent. The leaf disks were subsequently transferred to MS plates which contained 1.6% glucose, 2.0 mg/l zeatin riboside, 0.02 mg/l NAA, 0.02 mg/l GA3 (giberellic acid) and 500 mg/l claforan. Once the leaf disks had been incubated for 14 days, they were transferred to fresh plates. The first calluses appeared after about 6 to 7 weeks. Shoots which appeared were transferred to 250 ml glass flasks in which MS medium containing 3% sucrose and 0.5 mg/ml carbenicillin was present. The first roots appeared after about 14 days. The plants were subsequently cultivated under suitable conditions in a greenhouse.

Tomatoes were transformed essentially in accordance with the abovedescribed process.

DNA (Dellaporta et al., 1983) and RNA (Goodall et al., 1990 and Chomczynski and Sacchi, 1987) were isolated from the resulting plants by standard processes. It was possible to determine the integrity and the number of the transferred genes by DNA analysis ("Southern blot"), and to determine the amount of transcription by RNA analysis ("RNase protection" in accordance with Vankan and Filipowicz, 1988; Goodall and Filipowicz, 1989; Steinecke et al., 1992).

2.2 Protoplast isolation and PEG-mediated transformation

4–8 Week-old *Nicotiana tabacum* SR1 leaves from a sterile culture were cut off, cleaned with distilled $H_2O$, and placed in a 0.05% SDS solution in order to prevent bacterial contamination. The SDS was removed by washing twice with sterile $H_2O$, and the leaves were then equilibrated for 10 min in K3 medium (500 mg/l claforan, 1 mg/l NAA, 0.2 mg/l kinetin). After removing the central rib, the leaves were cut into pieces of 1–2 $cm^2$ in size. In order to isolate the mesophyll protoplasts, the leaf pieces were added to 30 ml of an enzyme solution containing cellulase and mazerozyme (1.5% cellulase, 0.5% mazerozym in K3 medium) in a sterile 1 l flask and exposed to a slight vacuum for 10 min. Following subsequent incubation at 27° C. for 16 h in the dark, the mixture was shaken for 30 min at 75 rpm. The protoplast suspension was then passed through steel sieves of 250 and 100 μm pore width, and the filtrate was divided between 12 ml centrifuged tubes and centrifuged for 5 min at 650 rpm in a Hettich Universal 2S centrifuge. The lower phase together with the sediment was sucked off using a 100 μm glass capillary, the protoplasts were washed with 10 ml of K3 medium, and the medium was sucked off once again after the centrifugation (see above) had been repeated. Subsequently, the protoplasts were taken up in W5 medium (154 mM NaCl, 125 mM $CaCl_2xH_2O$, 5 mM glucose, 5 mM KCl, pH 5.6), counted in a Fuchs-Rosenthal counting chamber, and then left to stand for 30 min in W5 medium. The protoplasts were separated off by centrifuging at 650 rpm for 5 min, and the sediment was then suspended in MaMg solution (450 mM mannitol, 15 mM $MgCl_2$, 0.1% MES, pH 5.6), the concentration of the suspension being adjusted to $1-3\times10^6$ protoplasts/ml. It was then possible to transfect the protoplasts directly or to store them for up to 4 h in a refrigerator.

For the transformation, the protoplasts were subjected to a 5-minutes heat shock at 45° C., while swirling occasionally, in a water bath, and then immediately cooled down to room temperature by being placed for 45 s in ice/water. Subsequently, 0.35 ml volumes of protoplast suspension were aliquoted into 10 ml centrifuge tubes and 50 μl of the DNA solution were then added to each of the tubes. 0.35 ml of PEG solution (100 mM $Ca(NO_3)_2 \times 4H_2O$, 400 mM mannitol, 40% PEG 4000, pH 7–9) was added dropwise after 10 min, and the transfection sample was then transferred to Petri dishes after a further 20 min during which all the samples were swirled for 5 min. Following the dropwise addition of 4 ml of K3 medium, the protoplasts were cultivated at 27° C. in the dark for 6–48 h. Following the incubation, the protoplasts were added to 12 ml centrifuge tubes, which were filled with sea water for washing and then centrifuged at 650 rpm for 3 min. The supernatant was removed down to 1 ml, and the protoplasts were then resuspended and transferred into Eppendorf tubes. After centrifuging at 13000 rpm (Biofuge) for 1 min and carefully removing the supernatant, the protoplasts were taken up in the relevant extraction buffers.

The DNA according to the invention were successfully introduced into protoplasts prepared by the abovedescribed method.

3. Examples of the elevated resistance of transgenic plants according to the invention 3.1 Elevated resistance toward phytopathogenic fungi The transgenic tobacco plants XL4, XL8, XL11, XL14, XL15 and XL19 which were listed under 2 (above), were selfed, and descendants of XL4 were chosen for the following test. The phytopathogenic fungus Botrytis cincera was used as the test pathogen.

(a) Test description

The tobacco plants were grown in a greenhouse at 23° C. and 70–80% relative atmospheric humidity until the beginning of the experiment. Water and fertilizers are supplied according to requirement. For the inoculation, the leaves of the 6–8 week-old plants were sprayed until dripping wet with a spore suspension of the pathogen. Subsequently, the plants were incubated under conditions which were favorable for the pathogen, i.e. at 20° C. and 100% relative atmospheric humidity. After 4 days, the health status of the plants was ascertained on the basis of infected leaf area in percent. A distinction was made between leaf stages (leaf 1=oldest leaf, leaf 6=youngest leaf).

| Plants (47 in each case) | 1–3 leaf | 4–6 leaf | Average |
|---|---|---|---|
| N. tabacum (wild type); % infected leaf areas | 22.4 | 24.0 | 23.2 |
| Transgenic plants; % infected leaf area | 14.3 | 17.1 | 15.7 |
| Reduction in infestation in % (in accordance with Abbott) | 36.3 | 29.0 | 32.5 |

3.2 Increased resistance toward viruses

The transgenic tobacco plants XL4, XL8, XL11, XL14, XL15 and XL19, which were listed under 2 (above), were selfed, and the homozygous descendants of XL4 (XL4.24) and XL8 (XL8.28) were chosen for the following test.

Various tospoviruses, and viruses of other families, were used as test pathogens.

(a) Test description

The tobacco plants were grown in a greenhouse at 23° C. and 70–80% relative atmospheric humidity until the beginning of the experiment. Water and fertilizers are supplied according to requirement.

3 g of leaf material from primarily infected leaves exhibiting clear viral symptoms were harvested from tobacco plants (Nicotiana rustica L.) which had been infected 3 weeks previously with the TSWV isolate L3 (DSM No.: PVO182), and then homogenized in a mortar in 30 ml of standard buffer (0.1 M Na-K phosphate buffer, pH 7.0 containing 0.2% polyvinylpyrrolidone MW 10000 and 0.2% (w/v) $Na_2SO_3$). This material was used undiluted and in a 1:25 dilution in the standard buffer, and 0.1 ml was then in each case applied, mechanically by abrasion, per leaf to each of 3 leaves of a test plant which was about 8–10 weeks old. The test plants had previously been dusted with an abrasive (carborundum, 600 mesh), and were rinsed with mains water once inoculation had taken place.

The development of symptoms on the plants was assessed visually from the 5th day after inoculation over a time period of 14 days using a rating scheme. Symptoms appear both on the infected leaves and systemically on non-infected leaves.

Step 0=no symptoms

Step 1=mild symptoms, annular spots on the leaves (necroses)

Step 2=severe symptoms, vein yellowing, mosaics, signs of die-back.

The rating values were used to elucidate the average rating value, which was then related to the rating values of the control plants.

In order further to quantify the resistance of the plants, a triple-antibody sandwich (TAS) ELISA process was used for determining the quantity of TSWV antigen. For this, Greiner microtiter plates (type 655001) were coated with 0.1 ml of polyclonal antiserum (DSM No., AS-0105, 2 μg/ml) per well. Using the standard ELISA buffer, pressed juices were prepared in dilutions of 1:30 and 1:500 from test-plant leaves which were primarily and secondarily infected. 3 Wells of the plate were in each case loaded with each sample (0.1 ml), and the plates were then incubated at 4° C. overnight. After the plates had been washed three times with PBS-Tween, 0.1 ml of a 1:1000 dilution of the two monoclonal antibodies 4F2 and 2B6 (Adam et al., 1991) was added to each well, and the plates were incubated at 37° C. for 3 h. After the plates had been washed three times with PBS-Tween, 0.1 ml of a 1:1000 dilution of a rabbit anti-mouse IgG conjugate (DAK Diagnostica GmbH, No.: D314) was added per well, and the plates were then incubated at 37° C. for 3 h. After the plates had been washed three times with PBS-Tween, the substrate p-nitrophenyl phosphate (1 mg/ml) was added, and the extinction at 405 nm was measured in a photometer after 30 min and after 1 h. The extinction values were used to determine the average extinction value, which was then related to the control measurements. The results demonstrate that the transgenic plants are without symptoms whereas the control plants exhibit severe symptoms. In addition to this, it is found that the quantity of the TSWV antigen in the transgenic plants, detected by reaction with the monoclonal antibody (Mab 2B6), is markedly lower than in the control plants.

(b) Test result

| Plants (in each case 4 × 10) | Severity of symptoms | Notes |
| --- | --- | --- |
| N. tabacum (wild type) | 2 | The control plants only grew to half the height of the transgenic plants. |
| Transgenic XL 4.24 | 0 | |
| Transgenic XL 8.28 | 0 | |

Biotest of XL 4.24 transgenic plants with various other tospovirus isolates (a) Test description Homozygous descendants of the transgenic plant XL4 (XL 4.24) were reared until they had reached the four-leaf stage.

The plants were randomly collected into groups of 20 and inoculated mechanically with homogenates from tobacco plants infected with various tospoviruses. The following virus isolates were used for the inoculation: TSWV-peanut= SA05 (DSM No. PV-0205); INSV (DSM No. PV-0280); INSV (DSM No. PV-0281). The plants used for isolating the inoculum had been inoculated 10–14 days previously and were, on the basis of electron microscopic findings, free from contamination with other viruses. In order to prepare the inoculum, the standard DSM inoculation buffer (DSM plant virus catalogue) was used, with the homogenisation being carried out using mortars and pestle and in the ratio 1:30 (g/ml). The inoculum was abraded, using sterile glass spatulas, on to the test-plant leaves which had been dusted with carborundum (600 mesh). The two oldest secondary leaves of each test plant were inoculated. After the inoculation, the infected leaves were rinsed with mains water. The plants were subsequently incubated under the abovementioned culture conditions and each day rated visually for symptoms. As controls, non-transformed *N. tabacum* plants were grown in the same way and inoculated with the various isolates.

The final ratings of the experiment were made by two observers at one and three weeks after the inoculation; in cases where the assessments differed, that which was less favorable was taken. The results are summarized in Table 1. Following successful infection, the TSWV-peanut (SA-05) isolate gave rise to local necroses on the infected leaves and to severe systemic symptoms, involving leaf deformation and necroses on the newly formed, systemically infected leaves, whereas the two INSV isolates only gave rise to the formation of local necroses on the inoculated leaves, without the occurrence of any systemic spread to newly formed leaves. When carrying out the rating in the case of TSWV-peanut, both systemically infected test plants and those which only exhibited local primary symptoms were taken to be successfully infected, since experience showed that in the latter case systemic symptoms were only delayed and would appear with time. In the case of the two INSV isolates, the appearance of local primary symptoms was alone taken as evidence of successful infection.

TABLE 1

Testing the transgenic tobacco line XL4 (XL4.24) for resistance toward TSWV-peanut and various other INSV isolates;

| Isolate | Infected control plants following mechanical inoculation | Infected transgenic plants following mechanical inoculation | Features of the infected plants |
|---|---|---|---|
| TSWV-Peanut = SA05 (DSM No. PV-0205) | 100% | 4% | Severe systemic infection |
| INSV = (DSM No. PV-0280) | 95% | 55% | Local lesions on the inoculated leaves; no systemic infection |
| INSV (DSM No. PV-0281) | 85% | 35% | Local lesions on the inoculated leaves; no systemic infection |

Biotest of XL 4.24 transgenic plants using virus isolates which do not belong to the bunyavirus family.

(a) Test description

Homozygous descendants of the transgenic plant XL4 (XL 4.24) were raised until they had reached the four-leaf stage.

The plants were randomly collected into groups of 20 and inoculated mechanically with homogenates from tobacco plants infected with various viruses. The following virus isolates were used for the inoculation: TMV (DSM No. PV-0055) and tobacco rattle virus (DSM No. PV-0043). The plants used for isolating the inoculum had been inoculated 10–14 days previously and were, on the basis of electron microscopic findings, free from contamination with other viruses. In order to prepare the inoculum, the standard DSM inoculation buffer (DSM plant virus catalogue) was used, with the homogenization being carried out using mortars and pestle and in the ratio 1:30 (g/ml). The inoculum was abraded, using sterile glass spatulas, onto the test-plant leaves, which had been dusted with carborundum (600 mesh). The two oldest secondary leaves of each test plant were inoculated. After the inoculation, the infected leaves were rinsed with mains water. The plants were subsequently incubated under the abovementioned culture conditions and each day rated visually for symptoms. As controls, non-transformed *N. tabacum* plants were grown in the same way and inoculated with the various isolates,.

The final ratings of the experiment were made by two observers at one and three weeks after the inoculation; in cases where the assessments differed, the less favorable was taken. While infection with both the viruses gave rise in the control plants to local necroses on the primarily infected leaves, that with TRV also gave rise to severe systemic symptoms. In the case of TMV, significantly fewer local lesions were observed in the transgenic XL4.24 plants. In the case of the tobacco rattle virus, 14% of the controls only had necroses on the primarily infected leaves, whereas 86% also exhibited systemic systems. By contrast, 28% of the transgenic plants were completely free of infection, 36% merely had primary necroses, and only 36% had systemic systems as well.

3.3 Elevated resistance toward phytopathogenic nematodes (a) Test description

The transgenic tobacco plants (XL4) were grown in a greenhouse at 23° C. and 70–80% relative atmospheric humidity until the beginning of the experiment. After pricking out, the plants were grown on in soil in order to ensure a particularly well-developed root system. Water and fertilizers were supplied according to requirement. Plants which were about 15 cm in height were inoculated by pipetting viable, freshly hatched larvae of *Meloidogyne incognita* (LII) uniformly on to the soil surface at the rate of about 300 larvae per 100 ml of soil volume. Rating took place 4 weeks after inoculation by determining the number of galls on each root system. In comparison to the wild type plants, the transgenic plants exhibit increased resistance toward nematodes.

In the present text, % values relate to percentages by weight, unless otherwise indicated, and dilutions to parts by volume (e.g. 1:25), unless otherwise indicated.

We claim:

1. DNA hybridizing under stringent hybridization conditions to a combination of fragment A linked directly or indirectly to fragment B, wherein:

fragment A consists of a double-stranded cDNA fragment derived from the RNA of the plum pox virus; and fragment B consists of a double-stranded cDNA fragment derived from the S RNA of the N structural gene of the tomato spotted wilt virus;

said hybridizing DNA, when expressed in a plant, conferring on said plant an increased resistance, as compared to a natural plant of the same species, to tomato spotted wilt virus and another virus selected from the group consisting of tospoviruses other than tomato spotted wilt virus, tobacco mosaic virus and tobacco rattle virus.

2. DNA according to claim 1, wherein fragment B is situated after fragment A in the 3' direction.

3. DNA according to claim 1, wherein fragment A comprises SEQ ID NO: 7 or a nucleotide sequence hybridizing thereto under stringent hybridization conditions.

4. DNA according to claim 3, wherein fragment A consists of SEQ ID NO: 7 or a nucleotide sequence hybridizing thereto under stringent hybridization conditions.

5. DNA according to claim 1, wherein fragment B comprises SEQ ID NO: 11 or a nucleotide sequence hybridizing thereto under stringent hybridization conditions.

6. DNA according to claim 5, wherein fragment B consists of SEQ ID NO: 11 or a nucleotide sequence hybridizing thereto under stringent hybridization conditions.

7. DNA according to claim 5, wherein fragment A comprises SEQ ID NO: 7 or a nucleotide sequence hybridizing thereto under stringent hybridization conditions.

8. DNA according to claim 7, wherein fragment A consists of SEQ ID NO: 7 or a nucleotide sequence hybridizing thereto under stringent hybridization conditions.

9. DNA according to claim 1, further comprising a promoter which is active in a plant.

10. DNA according to claim 9, wherein the promoter is the CaMV 35S promoter.

11. DNA according to claim 1, further comprising fragment C, which is a synthetic DNA sequence having 1 to 134 base pairs and which connects the open reading frame in fragment A to fragment B.

12. DNA according to claim 11, wherein fragment C comprises SEQ ID NO: 9.

13. DNA according to claim 12, wherein fragment C consists of SEQ ID NO: 9.

14. DNA according to claim 7, further comprising fragment D, which is a double-stranded DNA sequence having 1 to 30 base pairs and follows fragment B in the 3' direction.

15. DNA according to claim 14, wherein fragment D comprises SEQ ID NO: 13.

16. DNA according to claim 15, wherein fragment D consists of SEQ ID NO: 13.

17. DNA according to claim 1, further comprising a 3' untranslated DNA which follows fragment B directly in the 3' direction or is connected to fragment B through fragment D, which is a double-stranded DNA sequence having 1 to 30 base pairs.

18. DNA according to claim 17, wherein the 3' untranslated DNA comprises SEQ ID NO: 4.

19. DNA according to claim 18, wherein the 3' untranslated DNA consists of SEQ ID NO: 4.

20. A plasmid or phage vector containing DNA according to claim 1.

21. A transformed plant cell, said plant cell containing and expressing genomic DNA in addition to the DNA naturally constituting the genome of said plant cell, and said additional DNA comprising DNA according to claim 1, or propagation material of said transformed plant cell.

22. A transformed whole plant, said whole plant containing and expressing genomic DNA in addition to the DNA naturally constituting the genome of said whole plant, and said additional DNA comprising DNA according to claim 1, or propagation material of said transformed whole plant.

23. A transformed plant part, said plant part containing and expressing genomic DNA in addition to the DNA naturally constituting the genome of said plant part, and said additional DNA comprising DNA according to claim 1, or propagation material of said transformed plant part.

24. A method of protecting a plant against infection by tomato spotted wilt virus and another virus selected from the group consisting of tospoviruses other than tomato spotted wilt virus, tobacco mosaic virus and tobacco rattle virus, said method comprising transforming said plant with DNA according to claim 1 in a manner such that said DNA is expressed in an amount effective to protect said plant against said infection.

* * * * *

```
                              SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 1040 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 36..989

(xi) SEQUENCE DESCRIPTION: SEQ ID NO: 1:

AAAATATAAA AACTCAACAC AACATACAAA ATTTT ATG CAA TCA AAT CAA TCT          53
                                       Met Gln Ser Asn Gln Ser
                                        1               5

CAA GCT ATC AAA ATT TTT CGA ATC TCA CTT GAA AGA TCA AAA ATC AAC        101
Gln Ala Ile Lys Ile Phe Arg Ile Ser Leu Glu Arg Ser Lys Ile Asn
             10                  15                  20

AAA GAA AAT TCC TTA ATT TCT TTA CTA AAT TTA CTG CAA GTC AAG ATG        149
Lys Glu Asn Ser Leu Ile Ser Leu Leu Asn Leu Leu Gln Val Lys Met
            25                  30                  35

TCG AGA ATT CGA GCT CGG TAC CCA CCC GAT CCT CTA GAG TCG CAT ATA        197
Ser Arg Ile Arg Ala Arg Tyr Pro Pro Asp Pro Leu Glu Ser His Ile
        40                  45                  50

ACA ACT TCT ACA ATC ATC ATG TCT AAG GTT AAG CTC ACT AAG GAA AGC        245
Thr Thr Ser Thr Ile Ile Met Ser Lys Val Lys Leu Thr Lys Glu Ser
 55                  60                  65                  70

ATT GTT GCT TTG TTG ACA CAA GGC AAA GAC CTT GAG TTT GAG GAA GAT        293
Ile Val Ala Leu Leu Thr Gln Gly Lys Asp Leu Glu Phe Glu Glu Asp
                75                  80                  85

CAG AAT CTG GTA GCA TTC AAC TTC AAG ACT TTT TGT CTA GAA AAC CTC        341
Gln Asn Leu Val Ala Phe Asn Phe Lys Thr Phe Cys Leu Glu Asn Leu
            90                  95                 100

GAC CAG ATC AAG AAG ATG AGC GTT ATT TCA TGT CTG ACG TTC CTG AAG        389
Asp Gln Ile Lys Lys Met Ser Val Ile Ser Cys Leu Thr Phe Leu Lys
           105                 110                 115

AAT CGT CAG AGT ATA ATG AAG GTT ATT AAA CAA AGT GAT TTT ACT TTT        437
Asn Arg Gln Ser Ile Met Lys Val Ile Lys Gln Ser Asp Phe Thr Phe
       120                 125                 130

GGT AAA ATT ACC ATA AAG AAA ACT TCA GAC AGG ATT GGA GCC ACT GAC        485
Gly Lys Ile Thr Ile Lys Lys Thr Ser Asp Arg Ile Gly Ala Thr Asp
135                 140                 145                 150

ATG ACC TTC AGA AGG CTT GAT AGC TTG ATC AGG GTC AGG CTT GTA GAG        533
Met Thr Phe Arg Arg Leu Asp Ser Leu Ile Arg Val Arg Leu Val Glu
                155                 160                 165
```

```
GAA ACC GGG AAT TCT GAG AAT CTC AAT ACT ATC AAA TCT AAG ATT GCT        581
Glu Thr Gly Asn Ser Glu Asn Leu Asn Thr Ile Lys Ser Lys Ile Ala
            170                 175                 180

TCC CAC CCT TTG ATT CAA GCC TAT GGA TTA CCT CTT GAT GAT GCA AAG        629
Ser His Pro Leu Ile Gln Ala Tyr Gly Leu Pro Leu Asp Asp Ala Lys
            185                 190                 195

TCT GTG AGG CTT GCC ATA ATG CTG GGA GGT AGC TTA CCT CTT ATT GCT        677
Ser Val Arg Leu Ala Ile Met Leu Gly Gly Ser Leu Pro Leu Ile Ala
    200                 205                 210

TCA GTT GAT AGC TTT GAG ATG ATC AGT GTT GTC TTG GCT ATA TAT CAG        725
Ser Val Asp Ser Phe Glu Met Ile Ser Val Val Leu Ala Ile Tyr Gln
215                 220                 225                 230

GAT GCA AAA TAC AAA GAC CTC GGG ATT GAC CCA AAG AAG TAT GAC ACC        773
Asp Ala Lys Tyr Lys Asp Leu Gly Ile Asp Pro Lys Lys Tyr Asp Thr
                235                 240                 245

AAG GAA GCC TTA GGA AAA GTT TGC ACT GTG CTG AAA AGC AAA GCA TTT        821
Lys Glu Ala Leu Gly Lys Val Cys Thr Val Leu Lys Ser Lys Ala Phe
            250                 255                 260

GAA ATG AAT GAA GAT CAG GTG AAG AAA GGA AAA GAG TAT GCT GCT ATA        869
Glu Met Asn Glu Asp Gln Val Lys Lys Gly Lys Glu Tyr Ala Ala Ile
            265                 270                 275

CTC AGC TCC AGC AAT CCT AAT GCT AAA GGA AGT ATT GCT ATG GAA CAT        917
Leu Ser Ser Ser Asn Pro Asn Ala Lys Gly Ser Ile Ala Met Glu His
        280                 285                 290

TAC AGT GAA ACT CTT AAC AAG TTC TAT GAA ATG TTT GGG GTT AAA AAA        965
Tyr Ser Glu Thr Leu Asn Lys Phe Tyr Glu Met Phe Gly Val Lys Lys
295                 300                 305                 310

CAG GCA AAA CTC ACA GAA CTT GCT TAAAAGCAGT TGTAAGTTAA                  1009
Gln Ala Lys Leu Thr Glu Leu Ala
                315

ATTATGGAAA AGTCTACAAA TATATAAAGC T                                     1040

(2) INFORMATION FOR SEQ ID NO:2:

(i) SEQUENCE CHARACTERISTICS:
          (A) LENGTH: 318 amino acids
          (B) TYPE: amino acid
          (D) TOPOLOGY: linear (ii) MOLECULE TYPE: protein (xi) SEQUENCE DESCRIPTION: SEQ ID NO: 2:

Met Gln Ser Asn Gln Ser Gln Ala Ile Lys Ile Phe Arg Ile Ser Leu
 1               5                  10                  15

Glu Arg Ser Lys Ile Asn Lys Glu Asn Ser Leu Ile Ser Leu Leu Asn
                20                  25                  30

Leu Leu Gln Val Lys Met Ser Arg Ile Arg Ala Arg Tyr Pro Pro Asp
            35                  40                  45

Pro Leu Glu Ser His Ile Thr Thr Ser Thr Ile Met Ser Lys Val
    50                  55                  60

Lys Leu Thr Lys Glu Ser Ile Val Ala Leu Leu Thr Gln Gly Lys Asp
65                  70                  75                  80

Leu Glu Phe Glu Glu Asp Gln Asn Leu Val Ala Phe Asn Phe Lys Thr
                85                  90                  95

Phe Cys Leu Glu Asn Leu Asp Gln Ile Lys Lys Met Ser Val Ile Ser
            100                 105                 110

Cys Leu Thr Phe Leu Lys Asn Arg Gln Ser Ile Met Lys Val Ile Lys
        115                 120                 125

Gln Ser Asp Phe Thr Phe Gly Lys Ile Thr Ile Lys Lys Thr Ser Asp
    130                 135                 140
```

Arg Ile Gly Ala Thr Asp Met Thr Phe Arg Arg Leu Asp Ser Leu Ile
145                 150                 155                 160

Arg Val Arg Leu Val Glu Glu Thr Gly Asn Ser Glu Asn Leu Asn Thr
            165                 170                 175

Ile Lys Ser Lys Ile Ala Ser His Pro Leu Ile Gln Ala Tyr Gly Leu
            180                 185                 190

Pro Leu Asp Asp Ala Lys Ser Val Arg Leu Ala Ile Met Leu Gly Gly
            195                 200                 205

Ser Leu Pro Leu Ile Ala Ser Val Asp Ser Phe Glu Met Ile Ser Val
    210                 215                 220

Val Leu Ala Ile Tyr Gln Asp Ala Lys Tyr Lys Asp Leu Gly Ile Asp
225                 230                 235                 240

Pro Lys Lys Tyr Asp Thr Lys Glu Ala Leu Gly Lys Val Cys Thr Val
                245                 250                 255

Leu Lys Ser Lys Ala Phe Glu Met Asn Glu Asp Gln Val Lys Lys Gly
            260                 265                 270

Lys Glu Tyr Ala Ala Ile Leu Ser Ser Ser Asn Pro Asn Ala Lys Gly
            275                 280                 285

Ser Ile Ala Met Glu His Tyr Ser Glu Thr Leu Asn Lys Phe Tyr Glu
    290                 295                 300

Met Phe Gly Val Lys Lys Gln Ala Lys Leu Thr Glu Leu Ala
305                 310                 315

(2) INFORMATION FOR SEQ ID NO: 3:

(i) SEQUENCE CHARACTERISTICS:
        (A) LENGTH: 439 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 3:

AAGCTTGCAT GCCTGCAGGT CAACATGGTG GAGCACGACA CTCTCGTCTA        50

CTCCAAGAAT ATCAAAGATA CAGTCTCAGA AGACCAAAGG GCTATTGAGA        100

CTTTTCAACA AAGGGTAATA TCGGGAAACC TCCTCGGATT CCATTGCCCA        150

GCTATCTGTC ACTTGATCAA AAGGACAGTA GAAAAGGAAG GTGGCACCTA        200

CAAATGCCAT CATTGCGATA AGGAAAGGC TATCGTTCAA GAATGCCTCT         250

GCCGACAGTG GTCCCAAAGA TGGACCCCCA CCCACGAGGA GCATCGTGGA        300

AAAAGAAGAC GTTCCAACCA CGTCTTCAAA GCAAGTGGAT TGATGTGATA        350

TCTCCACTGA CGTAAGGGAT GACGCACAAT CCCACTATCC TTCGCAAGAC        400

CCTTCCTCTA TATAAGGAAG TTCATTTCAT TTGGAGAGG                    439

(2) INFORMATION FOR SEQ ID NO: 4:

(i) SEQUENCE CHARACTERISTICS:
        (A) LENGTH: 226 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 4:

CGCAAAAATC ACCAGTCTCT CTCTACAAAT CTATCTCTCT CTATTTTTCT         50

| | |
|---|---|
| CCAGAATAAT GTGTGAGTAG TTCCCAGATA AGGGAATTAG GGTTCTTATA | 100 |
| GGGTTTCGCT CATGTGTTGA GCATATAAGA AACCCTTAGT ATGTATTTGT | 150 |
| ATTTGTAAAA TACTTCTATC AATAAAATTT CTAATTCCTA AAACCAAAAT | 200 |
| CCAGTGACCT GCAGGCATGC AAGCTT | 226 |

(2) INFORMATION FOR SEQ ID NO: 5:

(i) SEQUENCE CHARACTERISTICS:
        (A) LENGTH: 1722 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 475..1428

(xi) SEQUENCE DESCRIPTION: SEQ ID NO: 5:

| | |
|---|---|
| AAGCTTGCAT GCCTGCAGGT CAACATGGTG GAGCACGACA CTCTCGTCTA | 50 |
| CTCCAAGAAT ATCAAAGATA CAGTCTCAGA AGACCAAAGG GCTATTGAGA | 100 |
| CTTTTCAACA AAGGGTAATA TCGGGAAACC TCCTCGGATT CCATTGCCCA | 150 |
| GCTATCTGTC ACTTGATCAA AAGGACAGTA GAAAAGGAAG GTGGCACCTA | 200 |
| CAAATGCCAT CATTGCGATA AAGGAAAGGC TATCGTTCAA GAATGCCTCT | 250 |
| GCCGACAGTG GTCCCAAAGA TGGACCCCCA CCCACGAGGA GCATCGTGGA | 300 |
| AAAAGAAGAC GTTCCAACCA CGTCTTCAAA GCAAGTGGAT TGATGTGATA | 350 |
| TCTCCACTGA CGTAAGGGAT GACGCACAAT CCCACTATCC TTCGCAAGAC | 400 |
| CCTTCCTCTA TATAAGGAAG TTCATTTCAT TTGGAGAGGA AAATATAAAA | 450 |
| ACTCAACACA ACATACAAAA TTTT ATG CAA TCA AAT CAA TCT CAA<br>                               Met Gln Ser Asn Gln Ser Gln<br>                                          5 | 495 |
| GCT ATC AAA ATT TTT CGA ATC TCA CTT GAA AGA TCA AAA ATC<br>Ala Ile Lys Ile Phe Arg Ile Ser Leu Glu Arg Ser Lys Ile<br>        10                  15                  20 | 537 |
| AAC AAA GAA AAT TCC TTA ATT TCT TTA CTA AAT TTA CTG CAA<br>Asn Lys Glu Asn Ser Leu Ile Ser Leu Leu Asn Leu Leu Gln<br>          25                  30                  35 | 579 |
| GTC AAG ATG TCG AGA ATT CGA GCT CGG TAC CCA CCC GAT CCT<br>Val Lys Met Ser Arg Ile Arg Ala Arg Tyr Pro Pro Asp Pro<br>        40                        45 | 621 |
| CTA GAG TCG CAT ATA ACA ACT TCT ACA ATC ATC ATG TCT AAG<br>Leu Glu Ser His Ile Thr Thr Ser Thr Ile Ile Met Ser Lys<br>50                  55                  60 | 663 |
| GTT AAG CTC ACT AAG GAA AGC ATT GTT GCT TTG TTG ACA CAA<br>Val Lys Leu Thr Lys Glu Ser Ile Val Ala Leu Leu Thr Gln<br>        65                  70                  75 | 705 |
| GGC AAA GAC CTT GAG TTT GAG GAA GAT CAG AAT CTG GTA GCA<br>Gly Lys Asp Leu Glu Phe Glu Glu Asp Gln Asn Leu Val Ala<br>          80                      85                  90 | 747 |
| TTC AAC TTC AAG ACT TTT TGT CTA GAA AAC CTC GAC CAG ATC<br>Phe Asn Phe Lys Thr Phe Cys Leu Glu Asn Leu Asp Gln Ile<br>          95                       100                105 | 789 |
| AAG AAG ATG AGC GTT ATT TCA TGT CTG ACG TTC CTG AAG AAT<br>Lys Lys Met Ser Val Ile Ser Cys Leu Thr Phe Leu Lys Asn<br>            110                      115 | 831 |

```
CGT CAG AGT ATA ATG AAG GTT ATT AAA CAA AGT GAT TTT ACT            873
Arg Gln Ser Ile Met Lys Val Ile Lys Gln Ser Asp Phe Thr
120                 125                 130

TTT GGT AAA ATT ACC ATA AAG AAA ACT TCA GAC AGG ATT GGA            915
Phe Gly Lys Ile Thr Ile Lys Lys Thr Ser Asp Arg Ile Gly
    135                 140                 145

GCC ACT GAC ATG ACC TTC AGA AGG CTT GAT AGC TTG ATC AGG            957
Ala Thr Asp Met Thr Phe Arg Arg Leu Asp Ser Leu Ile Arg
        150                 155                 160

GTC AGG CTT GTA GAG GAA ACC GGG AAT TCT GAG AAT CTC AAT            999
Val Arg Leu Val Glu Glu Thr Gly Asn Ser Glu Asn Leu Asn
                165                 170                 175

ACT ATC AAA TCT AAG ATT GCT TCC CAC CCT TTG ATT CAA GCC           1041
Thr Ile Lys Ser Lys Ile Ala Ser His Pro Leu Ile Gln Ala
                    180                 185

TAT GGA TTA CCT CTT GAT GAT GCA AAG TCT GTG AGG CTT GCC           1083
Tyr Gly Leu Pro Leu Asp Asp Ala Lys Ser Val Arg Leu Ala
190                 195                 200

ATA ATG CTG GGA GGT AGC TTA CCT CTT ATT GCT TCA GTT GAT           1125
Ile Met Leu Gly Gly Ser Leu Pro Leu Ile Ala Ser Val Asp
    205                 210                 215

AGC TTT GAG ATG ATC AGT GTT GTC TTG GCT ATA TAT CAG GAT           1167
Ser Phe Glu Met Ile Ser Val Val Leu Ala Ile Tyr Gln Asp
        220                 225                 230

GCA AAA TAC AAA GAC CTC GGG ATT GAC CCA AAG AAG TAT GAC           1209
Ala Lys Tyr Lys Asp Leu Gly Ile Asp Pro Lys Lys Tyr Asp
                235                 240                 245

ACC AAG GAA GCC TTA GGA AAA GTT TGC ACT GTG CTG AAA AGC           1251
Thr Lys Glu Ala Leu Gly Lys Val Cys Thr Val Leu Lys Ser
                    250                 255

AAA GCA TTT GAA ATG AAT GAA GAT CAG GTG AAG AAA GGA AAA           1293
Lys Ala Phe Glu Met Asn Glu Asp Gln Val Lys Lys Gly Lys
260                 265                 270

GAG TAT GCT GCT ATA CTC AGC TCC AGC AAT CCT AAT GCT AAA           1335
Glu Tyr Ala Ala Ile Leu Ser Ser Ser Asn Pro Asn Ala Lys
    275                 280                 285

GGA AGT ATT GCT ATG GAA CAT TAC AGT GAA ACT CTT AAC AAG           1377
Gly Ser Ile Ala Met Glu His Tyr Ser Glu Thr Leu Asn Lys
        290                 295                 300

TTC TAT GAA ATG TTT GGG GTT AAA AAA CAG GCA AAA CTC ACA           1419
Phe Tyr Glu Met Phe Gly Val Lys Lys Gln Ala Lys Leu Thr
                305                 310                 315

GAA CTT GCT TAAAAGCAGT TGTAAGTTAA ATTATGGAAA AGTCTACAAA           1468
Glu Leu Ala

TATATAAAGC TGGGGATCCT CTAGAGTCCG CAAAAATCAC CAGTCTCTCT           1518

CTACAAATCT ATCTCTCTCT ATTTTTCTCC AGAATAATGT GTGAGTAGTT           1568

CCCAGATAAG GGAATTAGGG TTCTTATAGG GTTTCGCTCA TGTGTTGAGC           1618

ATATAAGAAA CCCTTAGTAT GTATTTGTAT TTGTAAAATA CTTCTATCAA           1668

TAAAATTTCT AATTCCTAAA ACCAAAATCC AGTGACCTGC AGGCATGCAA           1718

GCTT                                                             1722
```

(2) INFORMATION FOR SEQ ID NO: 6:

(i) SEQUENCE CHARACTERISTICS:
        (A) LENGTH: 318 amino acids
        (B) TYPE: amino acid
        (D) TOPOLOGY: linear (ii) MOLECULE TYPE: protein (xi) SEQUENCE DESCRIPTION: SEQ ID NO: 6:

| | | | | | | | | | | | | | | |
|---|---|---|---|---|---|---|---|---|---|---|---|---|---|---|
Met Gln Ser Asn Gln Ser Gln Ala Ile Lys Ile Phe Arg Ile Ser Leu
1               5                   10                  15

Glu Arg Ser Lys Ile Asn Lys Glu Asn Ser Leu Ile Ser Leu Leu Asn
            20                  25                  30

Leu Leu Gln Val Lys Met Ser Arg Ile Arg Ala Arg Tyr Pro Pro Asp
        35                  40                  45

Pro Leu Glu Ser His Ile Thr Thr Ser Thr Ile Met Ser Lys Val
    50                  55                  60

Lys Leu Thr Lys Glu Ser Ile Val Ala Leu Leu Thr Gln Gly Lys Asp
65                  70                  75                  80

Leu Glu Phe Glu Glu Asp Gln Asn Leu Val Ala Phe Asn Phe Lys Thr
                85                  90                  95

Phe Cys Leu Glu Asn Leu Asp Gln Ile Lys Lys Met Ser Val Ile Ser
            100                 105                 110

Cys Leu Thr Phe Leu Lys Asn Arg Gln Ser Ile Met Lys Val Ile Lys
        115                 120                 125

Gln Ser Asp Phe Thr Phe Gly Lys Ile Thr Ile Lys Lys Thr Ser Asp
    130                 135                 140

Arg Ile Gly Ala Thr Asp Met Thr Phe Arg Arg Leu Asp Ser Leu Ile
145                 150                 155                 160

Arg Val Arg Leu Val Glu Glu Thr Gly Asn Ser Glu Asn Leu Asn Thr
                165                 170                 175

Ile Lys Ser Lys Ile Ala Ser His Pro Leu Ile Gln Ala Tyr Gly Leu
            180                 185                 190

Pro Leu Asp Asp Ala Lys Ser Val Arg Leu Ala Ile Met Leu Gly Gly
        195                 200                 205

Ser Leu Pro Leu Ile Ala Ser Val Asp Ser Phe Glu Met Ile Ser Val
    210                 215                 220

Val Leu Ala Ile Tyr Gln Asp Ala Lys Tyr Lys Asp Leu Gly Ile Asp
225                 230                 235                 240

Pro Lys Lys Tyr Asp Thr Lys Glu Ala Leu Gly Lys Val Cys Thr Val
                245                 250                 255

Leu Lys Ser Lys Ala Phe Glu Met Asn Glu Asp Gln Val Lys Lys Gly
            260                 265                 270

Lys Glu Tyr Ala Ala Ile Leu Ser Ser Ser Asn Pro Asn Ala Lys Gly
        275                 280                 285

Ser Ile Ala Met Glu His Tyr Ser Glu Thr Leu Asn Lys Phe Tyr Glu
    290                 295                 300

Met Phe Gly Val Lys Lys Gln Ala Lys Leu Thr Glu Leu Ala
305                 310                 315

(2) INFORMATION FOR SEQ ID NO: 7:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 36..152

(xi) SEQUENCE DESCRIPTION: SEQ ID NO: 7:

```
AAAATATAAA AACTCAACAC AACATACAAA ATTTT ATG CAA TCA AAT                47
                                      Met Gln Ser Asn

CAA TCT CAA GCT ATC AAA ATT TTT CGA ATC TCA CTT GAA AGA               89
Gln Ser Gln Ala Ile Lys Ile Phe Arg Ile Ser Leu Glu Arg
 5               10                  15

TCA AAA ATC AAC AAA GAA AAT TCC TTA ATT TCT TTA CTA AAT              131
Ser Lys Ile Asn Lys Glu Asn Ser Leu Ile Ser Leu Leu Asn
     20              25                  30

TTA CTG CAA GTC AAG ATG TCG                                          152
Leu Leu Gln Val Lys Met Ser
         35
```

(2) INFORMATION FOR SEQ ID NO: 8:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Gln Ser Asn Gln Ser Gln Ala Ile Lys Ile Phe Arg Ile Ser Leu
 1               5                  10                  15

Glu Arg Ser Lys Ile Asn Lys Glu Asn Ser Leu Ile Ser Leu Leu Asn
             20                  25                  30

Leu Leu Gln Val Lys Met Ser
             35
```

(2) INFORMATION FOR SEQ ID NO: 9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..36

(xi) SEQUENCE DESCRIPTION: SEQ ID NO: 9:

```
AGA ATT CGA GCT CGG TAC CCA CCC GAT CCT CTA GAG TC                    38
Arg Ile Arg Ala Arg Tyr Pro Pro Asp Pro Leu Glu
 1               5                  10
```

(2) INFORMATION FOR SEQ ID NO: 10:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO: 10:

```
Arg Ile Arg Ala Arg Tyr Pro Pro Asp Pro Leu Glu
 1               5                  10
```

(2) INFORMATION FOR SEQ ID NO: 11:

(i) SEQUENCE CHARACTERISTICS:
        (A) LENGTH: 850 base pairs
        (B) TYPE: nucleic acid
        (C) STRANDEDNESS: single
        (D) TOPOLOGY: linear (ii) MOLECULE TYPE: DNA (genomic)

(ix) FEATURE:
    (A) NAME/KEY: CDS
    (B) LOCATION: 2..799

(xi) SEQUENCE DESCRIPTION: SEQ ID NO: 11:

```
G CAT ATA ACA ACT TCT ACA ATC ATC ATG TCT AAG GTT AAG CTC ACT              46
  His Ile Thr Thr Ser Thr Ile Ile Met Ser Lys Val Lys Leu Thr
  1               5                   10                  15

AAG GAA AGC ATT GTT GCT TTG TTG ACA CAA GGC AAA GAC CTT GAG TTT             94
Lys Glu Ser Ile Val Ala Leu Leu Thr Gln Gly Lys Asp Leu Glu Phe
                20                  25                  30

GAG GAA GAT CAG AAT CTG GTA GCA TTC AAC TTC AAG ACT TTT TGT CTA            142
Glu Glu Asp Gln Asn Leu Val Ala Phe Asn Phe Lys Thr Phe Cys Leu
            35                  40                  45

GAA AAC CTC GAC CAG ATC AAG AAG ATG AGC GTT ATT TCA TGT CTG ACG            190
Glu Asn Leu Asp Gln Ile Lys Lys Met Ser Val Ile Ser Cys Leu Thr
        50                  55                  60

TTC CTG AAG AAT CGT CAG AGT ATA ATG AAG GTT ATT AAA CAA AGT GAT            238
Phe Leu Lys Asn Arg Gln Ser Ile Met Lys Val Ile Lys Gln Ser Asp
    65                  70                  75

TTT ACT TTT GGT AAA ATT ACC ATA AAG AAA ACT TCA GAC AGG ATT GGA            286
Phe Thr Phe Gly Lys Ile Thr Ile Lys Lys Thr Ser Asp Arg Ile Gly
80                  85                  90                  95

GCC ACT GAC ATG ACC TTC AGA AGG CTT GAT AGC TTG ATC AGG GTC AGG            334
Ala Thr Asp Met Thr Phe Arg Arg Leu Asp Ser Leu Ile Arg Val Arg
                100                 105                 110

CTT GTA GAG GAA ACC GGG AAT TCT GAG AAT CTC AAT ACT ATC AAA TCT            382
Leu Val Glu Glu Thr Gly Asn Ser Glu Asn Leu Asn Thr Ile Lys Ser
            115                 120                 125

AAG ATT GCT TCC CAC CCT TTG ATT CAA GCC TAT GGA TTA CCT CTT GAT            430
Lys Ile Ala Ser His Pro Leu Ile Gln Ala Tyr Gly Leu Pro Leu Asp
        130                 135                 140

GAT GCA AAG TCT GTG AGG CTT GCC ATA ATG CTG GGA GGT AGC TTA CCT            478
Asp Ala Lys Ser Val Arg Leu Ala Ile Met Leu Gly Gly Ser Leu Pro
    145                 150                 155

CTT ATT GCT TCA GTT GAT AGC TTT GAG ATG ATC AGT GTT GTC TTG GCT            526
Leu Ile Ala Ser Val Asp Ser Phe Glu Met Ile Ser Val Val Leu Ala
160                 165                 170                 175

ATA TAT CAG GAT GCA AAA TAC AAA GAC CTC GGG ATT GAC CCA AAG AAG            574
Ile Tyr Gln Asp Ala Lys Tyr Lys Asp Leu Gly Ile Asp Pro Lys Lys
                180                 185                 190

TAT GAC ACC AAG GAA GCC TTA GGA AAA GTT TGC ACT GTG CTG AAA AGC            622
Tyr Asp Thr Lys Glu Ala Leu Gly Lys Val Cys Thr Val Leu Lys Ser
            195                 200                 205

AAA GCA TTT GAA ATG AAT GAA GAT CAG GTG AAG AAA GGA AAA GAG TAT            670
Lys Ala Phe Glu Met Asn Glu Asp Gln Val Lys Lys Gly Lys Glu Tyr
        210                 215                 220

GCT GCT ATA CTC AGC TCC AGC AAT CCT AAT GCT AAA GGA AGT ATT GCT            718
Ala Ala Ile Leu Ser Ser Ser Asn Pro Asn Ala Lys Gly Ser Ile Ala
    225                 230                 235

ATG GAA CAT TAC AGT GAA ACT CTT AAC AAG TTC TAT GAA ATG TTT GGG            766
Met Glu His Tyr Ser Glu Thr Leu Asn Lys Phe Tyr Glu Met Phe Gly
240                 245                 250                 255

GTT AAA AAA CAG GCA AAA CTC ACA GAA CTT GCT TAAAAGCAGT                     809
Val Lys Lys Gln Ala Lys Leu Thr Glu Leu Ala
                260                 265

TGTAAGTTAA ATTATGGAAA AGTCTACAAA TATATAAAGC T                              850
```

(2) INFORMATION FOR SEQ ID NO: 12:

(i) SEQUENCE CHARACTERISTICS:
        (A) LENGTH: 266 amino acids
        (B) TYPE: amino acid
        (D) TOPOLOGY: linear (ii) MOLECULE TYPE: protein (xi) SEQUENCE DESCRIPTION: SEQ ID NO: 12:

```
His Ile Thr Thr Ser Thr Ile Ile Met Ser Lys Val Lys Leu Thr Lys
  1               5                  10                  15

Glu Ser Ile Val Ala Leu Leu Thr Gln Gly Lys Asp Leu Glu Phe Glu
                 20                  25                  30

Glu Asp Gln Asn Leu Val Ala Phe Asn Phe Lys Thr Phe Cys Leu Glu
             35                  40                  45

Asn Leu Asp Gln Ile Lys Lys Met Ser Val Ile Ser Cys Leu Thr Phe
 50                  55                  60

Leu Lys Asn Arg Gln Ser Ile Met Lys Val Ile Lys Gln Ser Asp Phe
 65                  70                  75                  80

Thr Phe Gly Lys Ile Thr Ile Lys Thr Ser Asp Arg Ile Gly Ala
                 85                  90                  95

Thr Asp Met Thr Phe Arg Arg Leu Asp Ser Leu Ile Arg Val Arg Leu
                100                 105                 110

Val Glu Glu Thr Gly Asn Ser Glu Asn Leu Asn Thr Ile Lys Ser Lys
                115                 120                 125

Ile Ala Ser His Pro Leu Ile Gln Ala Tyr Gly Leu Pro Leu Asp Asp
130                 135                 140

Ala Lys Ser Val Arg Leu Ala Ile Met Leu Gly Gly Ser Leu Pro Leu
145                 150                 155                 160

Ile Ala Ser Val Asp Ser Phe Glu Met Ile Ser Val Val Leu Ala Ile
                165                 170                 175

Tyr Gln Asp Ala Lys Tyr Lys Asp Leu Gly Ile Asp Pro Lys Lys Tyr
                180                 185                 190

Asp Thr Lys Glu Ala Leu Gly Lys Val Cys Thr Val Leu Lys Ser Lys
                195                 200                 205

Ala Phe Glu Met Asn Glu Asp Gln Val Lys Lys Gly Lys Glu Tyr Ala
210                 215                 220

Ala Ile Leu Ser Ser Ser Asn Pro Asn Ala Lys Gly Ser Ile Ala Met
225                 230                 235                 240

Glu His Tyr Ser Glu Thr Leu Asn Lys Phe Tyr Glu Met Phe Gly Val
                245                 250                 255

Lys Lys Gln Ala Lys Leu Thr Glu Leu Ala
                260                 265
```

(2) INFORMATION FOR SEQ ID NO: 13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

GGGGATCCTC TAGAGTC                                          17

(2) INFORMATION FOR SEQ ID NO: 14:

```
        (i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 14:

TGTGTTGAGT TTTTATATTT TCCTCTCCAA ATGAAA                                      36

(2) INFORMATION FOR SEQ ID NO: 15:

(i) SEQUENCE CHARACTERISTICS:
            (A) LENGTH: 5 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 15:

AGAGG                                                                         5

(2) INFORMATION FOR SEQ ID NO: 16:

(i) SEQUENCE CHARACTERISTICS:
            (A) LENGTH: 7 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 16:

AAAATAT                                                                       7

(2) INFORMATION FOR SEQ ID NO: 17:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 17:

GTCAGTGGCT CCAATCCTGT CTGAAG                                                 26

(2) INFORMATION FOR SEQ ID NO: 18:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 18:

TGTCGAGAAT TCGAGCTCGG TAC                                                    23
```